US006943165B2

(12) United States Patent
Bare et al.

(10) Patent No.: US 6,943,165 B2
(45) Date of Patent: *Sep. 13, 2005

(54) COMPOUND AND METHOD FOR THE TREATMENT OF PAIN

(75) Inventors: Thomas Michael Bare, West Chester, PA (US); Dean Gordon Brown, Wilmington, DE (US); Megan Murphy, Wilmington, DE (US); Rebecca Ann Urbanek, Wilmington, DE (US); Wenhua Xiao, Montreal (CA)

(73) Assignee: AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 10/934,753

(22) Filed: Sep. 3, 2004

(65) Prior Publication Data

US 2005/0101603 A1 May 12, 2005

Related U.S. Application Data

(63) Continuation of application No. 10/168,760, filed as application No. PCT/SE00/02611 on Dec. 19, 2000, now Pat. No. 6,787,547.

(60) Provisional application No. 60/236,783, filed on Sep. 29, 2000, provisional application No. 60/171,906, filed on Dec. 23, 1999.

(51) Int. Cl.$^7$ .................. A61K 31/495; A61K 31/50; A01N 43/58; A01N 43/60; C07D 237/26
(52) U.S. Cl. .................................. 514/248; 544/234
(58) Field of Search ................... 514/248; 544/234

(56) References Cited

U.S. PATENT DOCUMENTS 6,787,547 B2 * 9/2004 Bare et al. .................. 514/248

FOREIGN PATENT DOCUMENTS

WO          WO 95/11244        *   4/1995

* cited by examiner

*Primary Examiner*—Richard L. Raymond
*Assistant Examiner*—Zachary C. Tucker
(74) *Attorney, Agent, or Firm*—Kenneth F. Mitchell

(57) ABSTRACT

A compound, 7-chloro-4-hydroxy-2-(2-chloro-4-methylphenyl)-1,2,5,10-tetrahydropyridazino [4,5-b]quinoline-1,10-dione, pharmaceutically-acceptable salts thereof, a method for treating pain comprising administration of a pain-ameliorating effective amount of the compound and pharmaceutical compositions containing the compound.

16 Claims, No Drawings

COMPOUND AND METHOD FOR THE TREATMENT OF PAIN

RELATED APPLICATIONS

This is a Continuation of 10/168,760, filed Jan. 21, 2003, now U.S. Pat. No. 6,787,547, which is the National Phase of PCT Application No. PCT/SE00/02611, filed Dec. 19, 2000, which claims the priority of U.S. Provisional Application 60/171,906, filed Dec. 23, 1999 and 60/236,783, filed Sep. 29, 2000.

FIELD OF THE INVENTION

This invention relates to the treatment or prevention of pain or nociception.

RELATED ART

Pain is a sensory experience distinct from sensations of touch, pressure, heat and cold. It is often described by sufferers by such terms as bright, dull, aching, pricking, cutting or burning and is generally considered to include both the original sensation and the reaction to that sensation. This range of sensations, as well as the variation in perception of pain by different individuals, renders a precise definition of pain difficult, however, many individuals suffer with severe and continuous pain.

Pain that is caused by damage to neural structures is often manifest as a neural supersensitivity or hyperalgesia and is termed "neuropathic" pain. Pain can also be "caused" by the stimulation of nociceptive receptors and transmitted over intact neural pathways, such pain is termed "nociceptive" pain.

The level of stimulation at which pain becomes noted is referred to as the "pain threshold." Analgesics are pharmaceutical agents which relieve pain by raising the pain threshold without a loss of consciousness. After administration of an analgesic drug a stimulus of greater intensity or longer duration is required before pain is experienced. In an individual suffering from hyperalgesia an analgesic drug may have an anti-hyperalgesic effect. In contrast to analgesics, agents such as local anaesthetics block transmission in peripheral nerve fibers thereby blocking awareness of pain. General anaesthetics, on the other hand, reduce the awareness of pain by producing a loss of consciousness.

Tachykinin antagonists have been reported to induce antinociception in animals, which is believed to be analogous to analgesia in man (Maggi et al, J. Auton. Pharmacol. (1993) 13, 23–93). In particular, non-peptide NK-1 receptor antagonists have been shown to produce such analgesia. For example, the NK-1 receptor antagonist RP 67,580 produced analgesia with potency comparable to that of morphine (Garret et al, Proc. Natl. Acad. Sci. USA (1993) 88, 10208–10212).

The opioid analgesics are a well-established class of analgesic agents with morphine-like actions. Synthetic and semi-synthetic opioid analgesics are derivatives of five chemical classes of compound: phenanthrenes; phenylheptylamines; phenylpiperidines; morphinans; and benzomorphans. Pharmacologically these compounds have diverse activities, thus some are strong agonists at the opioid receptors (e.g. morphine); others are moderate to mild agonists (e.g. codeine); still others exhibit mixed agonist-antagonist activity (e.g. nalbuphine); and yet others are partial agonists (e.g. nalorphine). Whilst an opioid partial agonist such as nalorphine, (the N-alkyl analogue of morphine) will antagonize the analgesic effects of morphine, when given alone it can be a potent analgesic in its own right.

Of all of the opioid analgesics, morphine remains the most widely used, but, in addition to its therapeutic properties, it has a number of drawbacks including respiratory depression, decreased gastrointestinal motility (resulting in constipation), nausea and vomiting. Tolerance and physical dependence also limit the clinical uses of opioid compounds.

Aspirin and other salicylate compounds are frequently used in treatment to interrupt amplification of the inflammatory process in rheumatoid diseases and arthritis and temporarily relieve the pain. Other drug compounds used for these purposes include phenylpropionic acid derivatives such as Ibuprofen and Naproxen, Sulindac, phenyl butazone, corticosteroids, antimalarials such as chloroquine and hydroxychloroquine sulfate, and fenemates (J. Hosp. Pharm., 36:622 (May 1979)). These compounds, however, are ineffective for neuropathic pain.

Available therapies for pain also have drawbacks. Some therapeutic agents require prolonged use before an effect is experienced by the patient. Other existing drugs have serious side effects in certain patients, and subjects must be carefully monitored to ensure that any side effects are not unduly threatening. Most existing drugs provide only temporary relief from pain and must be taken consistently on a daily or weekly basis. With disease progression the amount of medication needed to alleviate the pain often increases, thus increasing the potential for adverse side effects.

NMDA receptors are defined by the binding of N-methyl-D-aspartate (NMDA) comprise a receptor/ion channel complex with several different identified binding domains. NMDA itself is a molecule structurally similar to glutamate (Glu) which binds at the glutamate binding suite and is highly selective and potent in activating the NMDA receptor (Watkins (1987); Olney (1989)).

Many compounds are known that bind at the NMDA/Glu binding site (for example CPP, DCPP-ene, CGP 40116, CGP 37849, CGS 19755, NPC 12626, NPC 17742, D-AP5, D-AP7, CGP 39551, CGP-43487, MDL-100,452, LY-274614, LY-233536, and LY233053). Other compounds, referred to as non-competitive NMDA antagonists, bind at other sites in the NMDA receptor complex (examples are phencyclidine, dizocilpine, ketamine, tiletamine, CNS 1102, dextromethorphan, memantine, kynurenic acid, CNQX, DNQX, 6,7-DCQX, 6,7-DCHQC, R(+)-HA-966, 7-chlorokynurenic acid, 5,7-DCKA, 5-iodo-7-chloro-kynurenic acid, MDL-28,469, MDL-100,748, MDL-29,951, L-689,560, L-687,414, ACPC, ACPCM, ACPCE, arcaine, diethylenetriamine, 1,10-diaminodecane, 1,12-diaminododecane, ifenprodil, and SL-82.0715). These compounds have been extensively reviewed by Rogawski (1992) and Massieu et. al., (1993), and articles cited therein.

In addition to its physiological function, glutamate (Glu) can be neurotoxic. Glu neurotoxicity is referred to as "excitotoxicity" because the neurotoxic action of Glu, like its beneficial actions, is mediated by an excitatory process (Olney (1990); Choi (1992)). Normally, when Glu is released at a synaptic receptor, it binds only transiently and is then rapidly removed from the receptor by a process that transports it back into the cell. Under certain abnormal conditions, including stroke, epilepsy and CNS trauma, Glu uptake fails and Glu accumulates at the receptor resulting in a persistent excitation of electrochemical activity that leads to the death of neurons that have Glu receptors. Many neurons in the CNS have Glu receptors, so excitotoxicity can cause an enormous amount of CNS damage.

Acute excitotoxicity injury can occur as a result of ischemic events, hypoxic events, trauma to the brain or spinal cord, certain types of food poisoning which involve an excitotoxic poison such as domoic acid, and seizure-mediated neuronal degeneration, which can result from persistent epileptic seizure activity (status epilepticus). A large body of evidence has implicated the NMDA receptor as one receptor subtype through which Glu mediates a substantial amount of CNS injury, and it is well established that NMDA antagonists are effective in protecting CNS neurons against excitotoxic degeneration in these acute CNS injury syndromes (Choi (1988); Olney (1990)).

In addition to neuronal damage caused by acute insults, excessive activation of Glu receptors may also contribute to more gradual neurodegenerative processes leading to cell death in various chronic neurodegenerative diseases, including Alzheimer's disease, amyotrophic lateral sclerosis, AIDS dementia, Parkinson's disease and Huntington's disease (Olney (1990)). It is generally considered that NMDA antagonists may prove useful in the therapeutic management of such chronic diseases.

In the 1980's it was discovered that PCP (also known as "angel dust") acts at a "PCP recognition site" within the ion channel of the NMDA Glu receptor. PCP acts as a non-competitive antagonist that blocks the flow of ions through the NMDA ion channel. More recently it has become evident that drugs which act at the PCP site as non-competitive NMDA antagonists are likely to have psychotomimetic side effects. Further, it is now recognized that certain competitive and non-competitive NMDA antagonists can cause similar pathomorphological effects in rat brain (Olney et. al., (1991); Hargreaves et. al., (1993)). Such compounds also have psychotomimetic effects in humans (Kristensen et. al., (1992); Herrling (1994); Grotta (1994)).

The glycine binding site of the NMDA receptor complex is distinguishable from the Glu and PCP binding sites. Also, it has recently been discovered that NMDA receptors occur as several subtypes which are characterized by differential properties of the glycine binding site of the receptor. Many compounds that bind at the NMDA receptor glycine site, useful for the treatment of stroke and neurodegenerative conditions, have been described in U.S. Pat. Nos. 5,604,227; 5,733,910; 5,599,814; 5,593,133; 5,744,471; 5,837,705 and 6,103,721.

SUMMARY OF THE INVENTION

It has now been discovered that a certain compound which exhibits the property of binding to the NMDA receptor glycine site has a utility for the amelioration of pain and particularly for the amelioration of neuropathic pain.

Therefore, in one aspect, the invention provides a compound, 7-chloro-4-hydroxy-2-(2-chloro-4-methylphenyl)-1,2,5,10-tetrahydropyridazino[4,5-b]quinoline-1,10-dione, according to structural diagram I;

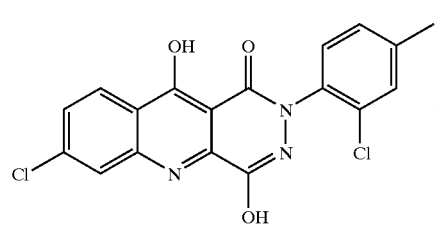

In another aspect, the invention provides a method for the treatment of pain using a compound in accord with structural diagram I, the method comprising administering a pain-ameliorating effective amount of the compound.

In another embodiment, the method comprises administration of a pain-ameliorating effective amount of the compound according to structural diagram I in the form of a pharmaceutical composition comprising a compound according to structural diagram I as an active ingredient together with one or more pharmaceutically-acceptable additives.

In a further embodiment, the method comprises binding the compound of the invention to the NMDA receptor glycine site of a warm-blooded animal, such as a human being, so as to beneficially inhibit the activity of the NMDA receptor.

Another aspect of the invention is a method for making the compound in accord with structural diagram I.

Yet other aspects of the invention are pharmaceutical compositions which contain the compound in accord with structural diagram I and the use of the compound in accord with structural diagram I for the preparation of medicaments and pharmaceutical compositions.

DETAILED DESCRIPTION OF THE INVENTION

The invention provides a compound, 7-chloro-4-hydroxy-2-(2-chloro-4-methylphenyl)-1,2,5,10-tetrahydropyridazino[4,5-b]quinoline-1,10-dione, pharmaceutically-acceptable salts thereof, methods of making the compound and its salts, pharmaceutical compositions containing the compound or salts thereof and methods for using the compound, the salts and the pharmaceutical compositions.

Suitable pharmaceutically-acceptable salts of compounds of the invention include acid addition salts such as methanesulphonate, fumarate, hydrochloride, hydrobromide, citrate, tris(hydroxymethyl)aminomethane, maleate and salts formed with phosphoric and sulphuric acid. In other embodiments, suitable salts are base salts such as an alkali metal salts for example sodium, alkaline earth metal salts for example calcium or magnesium, organic amine salts for example triethylamine, morpholine, N-methylpiperidine, N-ethylpiperidine, procaine, dibenzylamine, choline, N,N-dibenzylethylamine or amino acids such as lysine.

To use the compound of the invention or a pharmaceutically-acceptable salt thereof for the therapeutic treatment, which may include prophylactic treatment, of pain in mammals, which may be humans, the compound can be formulated in accordance with standard pharmaceutical practice as a pharmaceutical composition.

Suitable pharmaceutical compositions that contain a compound of the invention may be administered in conventional ways, for example by oral, topical, parenteral, buccal, nasal, vaginal or rectal administration or by inhalation. For these purposes a compound of the invention may be formulated by means known in the art into the form of, for example, tablets, capsules, aqueous or oily solutions, suspensions, emulsions, creams, ointments, gels, nasal sprays, suppositories, finely divided powders or aerosols for inhalation, and for parenteral use (including intravenous, intramuscular or infusion) sterile aqueous or oily solutions or suspensions or sterile emulsions. A preferred route of administration is orally by tablet or capsule.

In addition to a compound of the present invention a pharmaceutical composition of this invention may also contain one or more other pharmacologically-active agents, or such pharmaceutical composition may be simultaneously or sequentially co-administered with one or more other pharmacologically-active agents.

Pharmaceutical compositions of this invention will normally be administered so that a pain-ameliorating effective daily dose is received by the subject. The daily dose may be given in divided doses as necessary, the precise amount of the compound received and the route of administration depending on the weight, age and sex of the patient being treated and on the particular disease condition being treated according to principles known in the art. A preferred dosage regime is once daily.

A further embodiment of the invention provides a pharmaceutical composition which contains a compound of the invention as defined herein or a pharmaceutically-acceptable salt thereof, in association with a pharmaceutically-acceptable additive such as an excipient or carrier.

A yet further embodiment of the invention provide the use of the compound of the invention, or a pharmaceutically-acceptable salt thereof, in the manufacture of a medicament useful for binding to the NMDA receptor glycine site in a warm-blooded animal such as a human being.

Still another embodiment of the invention provides a method of binding the compound of the invention to the NMDA receptor glycine site of a warm-blooded animal, such as a human being, in need of treatment for pain, which method comprises administering to said animal an effective amount of a compound of structural diagram I or a pharmaceutically-acceptable salt thereof.

Definitions:

Generally in the methods, processes and examples described herein:

concentrations were carried out by rotary evaporation in vacuo;

operations were carried out at ambient temperature, that is in the range 18–26° C. and under a nitrogen atmosphere;

column chromatography (by the flash procedure) was performed on Merck Kieselgel silica (Art. 9385) unless otherwise stated;

yields are given for illustration only and are not necessarily the maximum attainable;

the structure of the end-products of the formula I were generally confirmed by NMR and mass spectral techniques, proton magnetic resonance spectra were determined in DMSO-$d_6$ unless otherwise stated using a Varian Gemini 2000 spectrometer operating at a field strength of 300 MHz; chemical shifts are reported in parts per million downfield from tetramethylsilane as an internal standard (δ scale) and peak multiplicities are shown thus: s, singlet; bs, broad singlet; d, doublet; AB or dd, doublet of doublets; t, triplet, dt, double of triplets, m, multiplet; bm, broad multiplet; fast-atom bombardment (FAB) mass spectral data were obtained using a Platform spectrometer (supplied by Micromass) run in electrospray and, where appropriate, either positive ion data or negative ion data were collected, in this application, $(M+H)_+$ is quoted;

intermediates were not generally fully characterized and purity was in general assessed mass spectral (MS) or NMR analysis.

The following abbreviations and definitions when used, have the meanings, as follows:

$CDCl_3$ is deuterated chloroform;

CMC is 1-cyclohexyl-3-(2-morpholinoethyl)carbodiimide metho-p-toluenesulfonate;

DCM is dichloromethane;

DCU is dicyclohexyl urea;

DHC is 1,3-dicyclohexylcarbodiimide;

DMAP is 4-(dimethylamino)pyridine;

DMF is N,N-dimethylformamide;

DMSO is dimethylsulphoxide;

m/s is mass spectroscopy;

NMP is N-methylpyrrolidinone;

NMR is nuclear magnetic resonance;

p.o. is per os;

THF is tetrahydrofuran, and t.i.d. is three times daily.

The examples and tests described herein are intended to illustrate but not limit the invention.

EXAMPLES

Example 1

The compound of the invention, 7-chloro-4-hydroxy-2-(2-chloro-4-methylphenyl)-1,2,5,10-tetrahydropyridazino[4,5-b]quinoline-1,10-dione, may be prepared by the following procedure:

2-Chloro-4-methyl Phenylhydrazine Hydrochloride

A suspension of 2-chloro-4-methyl aniline (10.1 mL, 11.63 g, 82.1 mmol) in 64 mL water and 60 mL 12 N HCl was cooled to −5° C. (internal temperature) and stirred with a mechanical stirrer. A solution of sodium nitrite (8.26 g, 119.7 mmol) in 56 mL water was added over 30 minutes. The solution became more clear but some solid remained. The mixture was stirred at −5° C. for 20 minutes and then cooled to −10° C. A solution of tin(II) chloride dihydrate (53.60 g, 237.6 mmol) in 36 mL 12 N HCl was added dropwise over 30 minutes while maintaining an internal temperature of −5 to −10° C. The resulting pinkish-brown mixture was stirred at −5 to −10° C. for 2 hours and then filtered cold through a pre-chilled fritted glass funnel. The collected solids were washed with cold 1% ethanol in ether (100 mL) followed by cold ether (500 μL) and air dried for 30 minutes. After drying in vacuo, the desired product was obtained as a very pale yellow crystalline solid (7.76 g, 49%). $^1$H NMR δ (300 MHz, $CDCl_3$) δ 10.09 (bs, 2H), 7.89 (s, 1H), 7.25 (dd, 1H, $J_m$=1.2 Hz), 7.13 (dd, 1H, $J_o$=8.4 Hz, $J_m$=1.2 Hz), 7.02 (d, 1H, $J_o$=8.4 Hz), 2.24 (s, 3H); MS (CI) m/z 157/159.

(tert-Butoxy)-N-[(2-chloro-4-methyl phenyl)amino]carboxamide

A suspension of 2-chloro-4-methylphenylhydrazine hydrochloride (7.74 g, 40.09 mmol) in 95 mL saturated aqueous NaHCO$_3$ was stirred for 10 minutes and then treated with solid K$_2$CO$_3$ (9.45 g, 68.37 mmol). The resulting fine light yellow suspension was stirred for 10 minutes. A solution of di-t-butyldicarbonate (12.97 g, 46.12 mmol) in 195 mL THF was added over 5 minutes and the resulting biphasic mixture was vigorously stirred for 3 hours. The reaction mixture was partitioned and the aqueous layer was extracted with ether (5×25 mL). The combined organic layers were washed with distilled water (2×75 mL), dried over MgSO$_4$, and concentrated under reduced pressure. Drying in vacuo afforded a light orange oil (14.07 g). The material was purified by flash chromatography on silica gel using 10:90 ether:hexanes as the eluant. The product was obtained as a light yellow oil which solidified upon standing (9.92 g, 96%). $^1$H NMR (300 MHz,CDCl$_3$) δ 8.88 (s, 1H), 7.15 (s, 1H), 7.09 (d, 1H, J$_m$=1.2 Hz), 6.97 (d, 1H, J$_o$=8.1 Hz), 6.64 (d, 1H, J$_o$=8.1 Hz), 2.18 (s, 3H), 1.41 (s, 9H); MS (CI) m/z 279/281.

Dimethyl 7-chloro-4-hydroxyquinoline-2,3-dicarboxylate

A stirred mixture of methyl 2-amino-4-chlorobenzoate (2.50 g, 13.5 mmol) and dimethyl acetylenedicarboxylate (2.05 g, 14.4 mmol) in tert-butanol (22 ml) was refluxed for 7 hours under a nitrogen atmosphere. After adding additional dimethyl acetylenedicarboxylate (1.16 g, 8.13 mmol) and refluxing another 2.5 hours, the reaction mixture was allowed to cool to room temperature and potassium tert-butoxide (1.56 g, 13.9 mmol) was added in one portion. A precipitate formed and the resulting mixture was refluxed for 1.5 hours. The mixture was cooled to room temperature and filtered to separate the solids, which were washed with tert-butanol and ether. The solids were dissolved in water and acidified with 1 N sulfuric acid to form a precipitate. The resulting mixture was extracted with methylene chloride and the combined extracts were washed with brine and water, dried over MgSO$_4$, filtered and concentrated to give a green solid. Recrystallization of this material from methanol provided the title compound (1.15 g, 47%) as an off-white solid, mp 232–233° C.; MS (CI):296 (M+H). Analysis for C$_{13}$H$_{10}$ClNO$_5$: Calc'd: C, 52.81; H, 3.41; N, 4.74; Found: C, 52.75; H, 3.47; N, 4.69.

3-Carbomethoxy-7-chloro-4-hydroxyquinoline-2-carboxylic acid

To a stirred suspension of dimethyl 7-chloro-4-hydroxyquinoline-2,3-dicarboxylate (1.0 g, 3.38 mmol) in water (20 mL) was added an aqueous solution of sodium hydroxide (0.27 g, 6.75 mmol). Upon addition, the suspension dissolved. The reaction mixture was warmed to 60° C. for 1 hour. After this time the reaction was cooled to room temperature and acidified with concentrated hydrochloric acid. The product was then extracted into diethyl ether and ethyl acetate. The organic extracts were dried over MgSO$_4$, filtered and concentrated in vacuo to provide the title compound as a solid (900 mg). This material was purified by recrystalization employing an ethyl acetate/hexane co-solvent system to provide the title compound (571 mg, 60%) as a white solid mp 296° C. (dec); MS (CI)=238 (M+H). Analysis for C$_{12}$H$_8$NO$_5$Cl.0.45 CH$_3$CO$_2$CH$_2$CH$_3$.0.10H$_2$O: Calc'd: C, 51.30; H, 3.68; N 4.34, Found: C, 51.28; H, 3.62; N 3.97 $^1$H NMR 8.22 (d, J=8.7 Hz, 1H), 7.92 (d, J=1.8 Hz, 1H), 7.28 (dd, J=8.7, 1.8 Hz, 1H), 3.90 (s, 3H).

3-Carbomethoxy-2-pyrrolidinocarbamide-7-chloro-4-hydroxyquinoline

To a suspension of 3-carbomethoxy-7-chloro-4-hydroxyquinoline-2-carboxylic acid 2.25 g, 8.0 mmol) in THF (20 mL) at ambient temperature under a N$_2$ atmosphere was added dicyclohexylcarbodiimide (1.65 g, 8.0 mmol) and pyrrolidine (0.596 g, 8.4 mmol). The reaction as stirred room temperature for 15 hours after which time the by-product urea was removed via filtration. The desired product was purified via flash column chromatography employing 5% methanol in chloroform to provide the title compound (2.52 g, 94.3%) as a tan solid, mp=215° C.; MS (CI): 335 (M+H). 300 MHz $^1$H NMR (DMSO-d$_6$): 8.12 (d, J=8.7 Hz, 1H), 7.60 (d, 1H, J=1.8 Hz), 7.47 (dd, 1H, J=8.8, 2.0 Hz), 3.69 (s, 3H), 3.40–3.49 (m, 2H), 3.27–3.33 (m, 2H), 1.80–1.96 (m, 4H).

7-Chloro-4-oxo-2-(pyrrolidinylcarbonyl)hydroquinoline-3-carboxylic acid

To a suspension of 3-carbomethoxy-2-pyrrolidinocarbamide-7-chloro-4-hydroxy quinoline (2.52 g, 7.5 mmol) in de-ionized water (40 mL) was added dropwise a solution (20 mL) of an aqueous potassium hydroxide (882 mg, 15.75 mmol). Upon complete addition, the reaction was warmed to 60° C. After 3 hours, the reaction was filtered to remove a small amount of insoluble material. The filtrate was then acidified to pH=1 which yield a white precipitate. The solid was isolated by vacuum filtration, washed with water, and dried at 30° C. in vacuo for 16 hours. This provided the title compound (1.5 g, 64%) as a white solid, mp= 225–8° C.; MS (CI): 321 (M+H). 300 MHz $^1$H NMR (DMSO-d$_6$): 8.28 (d, J=8.8 Hz, 1H), 7.77 (s, 1H), 7.64 (d, 1H, J=8.7), 3.52–3.57 (m, 2H), 3.17–3.19 (m, 2H), 1.83–1.98 (m, 4H).

N-[(tert-butoxy)carbonylamino][7-chloro-4-oxo-2-(pyrrolidinylcarbonyl)(3-hydroquinolyl)]-N-(2-chloro-4-methyl phenyl)carboxamide To a stirred suspension of 7-chloro-4-oxo-2-(pyrrolidinylcarbonyl)hydroquinoline-3-carboxylic acid (14.57 g, 45.43 mmol) in anhydrous THF (300 mL) under nitrogen was added 1-cyclohexyl-3-(2-morpholinoethyl)carbodiimide metho-p-toluenesulfonate (CMC, 34.89 g, 82.37 mmol). The white suspension immediately became bright yellow. The (tert-butoxy)-N-[ (2-chloro-4-methyl phenyl)amino]carboxamide (13.89 g, 54.10 mmol) was added as a solid followed by 50 mL anhydrous THF. The bright yellow reaction mixture was stirred at room temperature for 22 hours. A second portion of CMC (16.77 g, 39.59 mmol) was added to the reaction mixture. After 2.5 hours at room temperature, the reaction was heated at 60° C. for 5.5 hours. After cooling to room temperature, the reaction mixture was filtered and the collected solids were washed with THF. The filtrate and washes were concentrated and dried in vacuo to afford a light yellow foam. The material was dissolved in methylene chloride (400 mL), washed with distilled water (2×150 mL), and extracted with 10% NaHCO$_3$ (2×500 mL). The organic layer was dried over Na$_2$SO$_4$, concentrated and dried in vacuo to afford a light tan foam. The material was purified by flash chromatography on silica gel using a gradient of 95:5 to 85:15 chloroform:methanol as eluant to afford 15.42 g (61%) of the desired product as a white solid. $^1$H NMR (300 MHz, DMSO, d$_6$) δ 13.03 (bs, 1H), 9.19 (bs, 1H), 8.25 (d, 1H, J$_o$=8.7 Hz), 7.68 (d, 1H, J$_m$=1.8 Hz), 7.54 (dd, 1H, J$_0$=8.7 Hz, J$_m$=1.8 Hz), 7.50 (d, 1H, J$_m$=1.8 Hz), 7.45 (d, 1H, J$_0$=7.8 Hz), 6.81 (d, 1H, J$_o$=7.8 Hz), 3.47 (m, 4H), 2.34 (s, 3H), 1.90 (m, 4H), 1.40 (s, 9H); MS (−CI) m/z 559/561.

7-Chloro-4-hydroxy-2-(2-chloro-4-methyl phenyl)-1,2,5,10-tetrahydropyridazino[4,5-b] quinoline-1,10-dione To a stirred suspension of N-[(tert-butoxy)carbonylamino][7-chloro-4-oxo-2-(pyrrolidinylcarbonyl)(3-hydroquinolyl)]-N-(2-chloro-4-methyl phenyl)carboxamide (21.16 g, 37.82 mmol) in 900 mL anhydrous THF under nitrogen was slowly added methanesulfonic acid (120.0 mL, 184.9 mmol). The resulting dark yellow solution was stirred at room temperature for 18 hours. The solution was poured into 7 L water, stirred 3 hours, and filtered to afford a light yellow solid. The solid was sonicated in methanol, isolated by filtration, and dried in vacuo (30 mm) at 40° C. to afford the product as a white solid (12.93 g, 88%). $^1$H NMR (300 MHz, DMSO, d$_6$) δ 12.90 (bs, 1H), 12.10 (bs, 1H), 8.16 (d, 1H, J$_o$=8.7 Hz), 8.07 (d, 1H, J$_m$=1.8 Hz), 7.47 (dd, 1H, J$_o$=8.7 Hz, J$_m$=1.8 Hz), 7.47 (d, 1H, J$_m$=1.2 Hz), 7.42 (d, 1H, J$_o$=8.1 Hz), 7.29 (dd, 1H, J$_o$=8.1 Hz, J$_m$=1.2 Hz), 2.38 (s, 3H); MS (CI) m/z 388/390/392. Calc'd. for C$_{18}$H$_{11}$Cl$_2$N$_3$O$_3$: C, 55.69; H, 2.86; N, 10.82. Found C, 55.78; H, 2.89; N, 10.79.

Example 2

7-chloro-4-hydroxy-2-(2-chloro-4-methylphenyl)-1,2,5,10-tetrahydropyridazino[4,5-b]quinoline-1,10-dione choline salt A suspension of 7-chloro-4-hydroxy-2-(2-chloro-4-methyl phenyl)-1,2,5,10-tetrahydropyridazine[4,5-b]quinoline-1,10-dione (753 mg, 1.94 mmol) in methanol (50 mL) was treated with choline hydroxide (550 mL of a 45% solution in methanol, 1.94 mmol). Most of the solids dissolved immediately and the mixture was sonicated for 10 min to dissolve the rest. The solution was filtered through a 0.2 micron nylon syringe filter. The solution was reduced by rotary evaporation to 1.01 g (>100%) yellow solid. The solid was recrystallized from refluxing ethanol (25 mL), and the solution was allowed to crystallize slowly and without agitation. After about 2 h, the crystals were collected by vacuum filtration. The yellow solid was air dried to give (696 mg, 73%) of the title compound, which was recrystallized from refluxing ethanol (20 mL). Solids were allowed to form over 16 h, and were gently scraped from the flask and collected by vacuum filtration and washed with ethanol (2×3 mL) to afford 500 mg of the title compound, which upon drying at 100 mTorr at 30° C. for three days provided 480 mg of the title compound (50%). mp 239.5–240.5° C. (decomp.); $^1$H NMR (300 MHz, DMSO-d$_6$) δ 8.12–8.09 (2H, m); 7.34–7.17 (4H, m); 3.86–3.80 (2H, m); 3.39 (2H, t, J=5.25 Hz); 3.09 (9H, s); 2.35 (3H, s); Calc'd. for C$_{18}$H$_{10}$N$_3$O$_3$Cl$_2$.1.0 C$_5$H$_{14}$NO.0.6H$_2$O: C, 55.01; H, 5.06; N, 11.16; Found, C, 55.04, 54.75; H, 4.86, 4.86; N, 11.05, 11.07.

Biological Function Tests

Test A: Inhibition of binding of [$^3$H]-MDL105,519:

Rat Brain Membranes: The rat brain membranes used in the experiments were obtained from Analytical Biological Services Inc., and were prepared substantially in accordance with the method of B. M. Baron et al., *J. Pharmacol. Exp. Ther.* 250, 162 (1989). Briefly, fresh brain tissue including cerebral cortex and hippocampus from male Sprague Dawley rats was homogenized in 0.32 M sucrose and centrifuged at low speed to separate cellular membranes from other cellular components. The membranes were then washed 3 times using deionized water, followed by treatment with 0.04% Triton X-100. Finally, membranes were washed six times in 50 mM Tris citrate buffer, pH 7.4, and frozen at −80° C. until use.

[$^3$H]MDL105,519 (72 Ci/mmol) was purchased from Amersham. Cold MDL105,519 was purchased from Sigma/RBI. Binding assays were performed substantially in accordance with the protocol of B. M. Baron et al.,*J. Pharmacol. Exp. Ther.* 279, 62 (1996), as follows. On the day of the experiment, brain membranes were thawed at room temperature and suspended in 50 mM tris acetate buffer, pH 7.4 ("TAB"). Seventy-five micro grams per milliliter protein (by using the BioRad dye) were used for competition binding. The experiments were carried out using 96-well plates. Membranes were incubated with 20 μL of compounds of various concentrations and 1.2 nM [$^3$H]MDL105,519 for 30 minutes at room temperature in a total volume of 250 μL. Non specific binding was determined by using 100 μM of unlabeled MDL105,519. The unlabeled MDL105,519 and compounds were dissolved as 12.5 mM stock solutions in DMSO. Final DMSO concentration in each well was kept below 1%, which concentration was found not to alter the binding results. After incubation, unbound [$^3$H]MDL105,519 was removed by filtration onto GF/B Unifilter plates using a Packard harvester. Filters were washed four times with ice cold TAB (total of 1.2 mL buffer). The plates were dried overnight at room temperature and bound radioactivity was measured on a Packard TopCount after the addition of 45 μL per well of the MICROSCINT O. Potency of a compound is expressed as the Ki and results were calculated using Microsoft Excel spreadsheet and GraphPad Prizm software.

Human Brain Membranes: Human brain membranes were obtained from Analytical Biological Services Inc., and assays were performed as described for rat membranes.

Test B: Formalin Test:

The Formalin test assesses the inhibitory effects of orally administered compounds on formalin-induced nociceptive behaviors in rats (D. Dubuisson, et al., *Pain* 4, 161–174 (1977); H. Wheeler-Aceto et al., *Psychopharmacology* 104, 35–44 (1991); T. J. Coderre, et al., *Pain* 54, 43–50 (1993)). In the test two distinctive phases of formalin-induced behaviors are detected. A first phase response, caused by acute nociception to the noxious chemical (formalin) injected into the paw, occurs between 0 to 5 minutes. A quiescent period of between 5 to 15 min post injection follows. After the quiescent period a second phase response, caused by sensitization of the central neurons in the dorsal horn, occurs after 15 minutes and lasts up to 60 minutes. Central sensitization augments a noxious afferent input causing a stronger pain barrage to be transmitted to the brain. Inhibition of the second phase response indicates a spinal mechanism of drug action.

The procedure for the formalin test is as follows: male rats are placed in a plexiglass chamber and observed for 30–45 min. to observe their baseline activity. Multiple groups of animals are pretreated with either vehicle or different doses of a test compound. Animals are dosed 3 hours prior to injection of formalin into a hind paw (under the dorsal skin) with 0.05 mL of sterile 1% formalin. The number of paw flinches (responses) during first phase (0–5 min.) and second phase (20–35 min.) are scored and recorded. Flinch response is calculated as percentage of inhibition compared with the mean score of a saline control group. The $ED_{50}$ is the dose of compound which produces 50% inhibition of nociceptive response.

% inhibition of nociceptive response= 100×(number of responses in vehicle group−number of responses in compound group)(number of responses in vehicle group)

Student's t-test was used for statistical analysis to determine the significance of compound effects. Compounds are considered active based on their ability to inhibit flinch responses.

Test C: Neuropathic Pain Model (Chronic Constriction Injury):

The Chronic Constriction Injury ("CCI") test models neuropathic pain associated with nerve injuries that can arise directly from trauma and compression, or indirectly from a wide range of diseases such as infection, cancer, metabolic conditions, toxins, nutritional deficiencies, immunological dysfunction, and musculoskeletal changes. In the model a unilateral peripheral hyperalgesia is produced in rats by nerve ligation (G. J. Bennett, et al., *Pain* 33, 87–107 (1988)).

Procedurally, Sprague-Dawley rats (250–350 g) are anesthetized with sodium pentobarbital and the common sciatic nerve is exposed at the level of the mid thigh by blunt dissection through the biceps femoris. A section of nerve (about 7 mm), proximal to the sciatic trifucation, is freed of tissue and ligated at four positions with chromic gut suture. The suture is tied with about 1 mm spacing between ligatures. The incision is closed in layers and the animals are allowed to recuperate. Thermal hyperalgesia is measured using a paw-withdrawal test (K. Hargreaves, et al., *Pain* 32, 77–88 (1988)). To perform the test, animals are habituated on an elevated glass floor. A radiant heat source is aimed at the mid-plantar hindpaw (sciatic nerve territory) through the glass floor with a 20 second cut-off used to prevent injury to the skin. The latencies for the withdrawal reflex in both hind paws are recorded.

Injured paws with ligated nerves show shorter paw withdrawal latencies compared to the uninjured or sham operated paws. Response to test compounds are evaluated at different times after oral administration to determine onset and duration of compound effect. Dose response studies are conducted with multiple groups of CCI rats dosed orally with either vehicle or the test compound three times daily with either vehicle or the test compound for 5 days. Paw withdrawal latencies are measured each day 10 min before and 2 or 3 hr after the first daily dose. Efficacy is calculated as mean percentage decrease of hyperalgesia over 5 dosing days compared to vehicle-treated group. Compound potencies are expressed as the minimum effective dose (MED) in mg/Kg/day that yields a % decrease in hyperalgesia that is statistically significant, where the anti-hyperalgesic effect is determined as follows:

% of anti-hyperalgesia =
$$\frac{\text{(Mean of vehicle group} - \text{Mean of compound group)}}{\text{(Mean of vehicle group)}} \times 100$$

Data analysis was performed by multiple means comparison (Dunnett's test).

Table 1 shows the results from Tests A, B and C for the compound of the invention.

TABLE 1

| Test: | Result: |
|---|---|
| A: Affinity for NMDA glycine site (Inhibition of $^3$H-MDL-105519 binding) | 56 nM (rat brain) 50 nM (human brain) |
| B: Efficacy in formalin pain model | $ED_{50}$~100 mg/Kg |
| C: CCI model of neuropathic pain, heat hyperalgesia. | 65% anti-hyperalgesia at MED < 2 mg/Kg/d |

In the Formalin pain model the effective dose the compound of the invention that caused a 50% decrease in sensitivity to a painful stimulus was about 100 mg/Kg which dose was comparable to the dose of gabapentin required to achieve a similar result. In the CCI model of neuropathic pain, however, the minimal effective dose of the compound of the invention was less than 2 mg/Kg/day to achieve 65% anti-hyperalgesia. In comparison, about 90 mg/Kg/day of gabapentin is required to achieve about 46% anti-hyperalgesia.

When administered by intrathecal injection, the compound of the invention inhibited the development of NMDA induced behavior/seizure with an $ED_{50}$ of 110 nmol.

The compound of the invention was also tested for binding to a panel of more than 80 non-NMDA receptors. The compound showed no significant interaction with any tested receptor other than the NMDA receptor.

What is claimed is:

1. 7-Chloro-4-hydroxy-2-(2-chloro-4-methylphenyl)-1,2,5,10-tetrahydropyridazino[4,5-b]quinoline-1,10-dione.

2. A pharmaceutically-acceptable salt of a compound according to claim 1, selected from:
   acid addition salts selected from methanesulphonate, fumarate, hydrochloride, hydrobromide, citrate, tris(hydroxymethyl)aminomethane, maleate and salts formed with phosphoric and salts formed with sulphuric acid;
   alkali metal salts selected from sodium, calcium or magnesium;
   organic amine salts selected from triethylamine, morpholine, N-methylpiperidine, N-ethylpiperidine, procaine, dibenzylamine, choline, N,N-dibenzylethylamine or lysine.

3. A pharmaceutically-acceptable salt according to claim 2, selected from methanesulphonate, fumarate, hydrochloride, citrate, maleate, morpholine and choline.

4. A pharmaceutically-acceptable salt according to claim 3, which is a choline salt.

5. A pharmaceutical composition comprising a pain-ameliorating effective amount of a compound according to claim 1 as an active ingredient together with one or more pharmaceutically-acceptable additives, excipients or diluents.

6. A pharmaceutical composition comprising a pain-ameliorating effective amount of a compound according to claim 2 as an active ingredient together with one or more pharmaceutically-acceptable additives, excipients or diluents.

7. A pharmaceutical composition comprising a pain-ameliorating effective amount of a compound according to claim 3 as an active ingredient together with one or more pharmaceutically-acceptable additives, excipients or diluents.

8. A pharmaceutical composition comprising a pain-ameliorating effective amount of a compound according to claim 4 as an active ingredient together with one or more pharmaceutically-acceptable additives, excipients or diluents.

9. A method for treating neuropathic pain, said method comprising administration of a pain-ameliorating effective amount of the compound according to claim 1.

10. A method for treating neuropathic pain, said method comprising administration of a pain-ameliorating effective amount of a pharmaceutically-acceptable salt according to claim 2.

11. A method for treating neuropathic pain, said method comprising administration of a pain-ameliorating effective amount of a pharmaceutically-acceptable salt according to claim 3.

12. A method for treating neuropathic pain, said method comprising administration of a pain-ameliorating effective amount of a pharmaceutically-acceptable salt according to claim 4.

13. A method for treating neuropathic pain, said method comprising administration of a pain-ameliorating effective amount of a pharmaceutical composition according to claim 5.

14. A method for treating neuropathic pain, said method comprising administration of a pain-ameliorating effective amount of a pharmaceutical composition according to claim 6.

15. A method for treating neuropathic pain, said method comprising administration of a pain-ameliorating effective amount of a pharmaceutical composition according to claim 7.

16. A method for treating neuropathic pain, said method comprising administration of a pain-ameliorating effective amount of a pharmaceutical composition according to claim 8.

\* \* \* \* \*